United States Patent
McGee et al.

(10) Patent No.: US 7,332,462 B2
(45) Date of Patent: Feb. 19, 2008

(54) MALODOR COUNTERACTANT COMPOUNDS

(75) Inventors: Thomas McGee, Nanuet, NY (US); Kenneth Leo Purzycki, Lake Parsippany, NJ (US); Venkateswara Kumar Vedantam, Jalan Lempeng (SG); Tee Yong Tan, Eunos Crescent (SG); John Callf, Singapore (SG)

(73) Assignee: Givaudan SA, Vernier (CH)

( * ) Notice: Subject to any disclaimer, the term of this patent is extended or adjusted under 35 U.S.C. 154(b) by 0 days.

(21) Appl. No.: 11/626,047

(22) Filed: Jan. 23, 2007

(65) Prior Publication Data

US 2007/0116655 A1    May 24, 2007

Related U.S. Application Data

(62) Division of application No. 11/202,718, filed on Aug. 12, 2005, which is a division of application No. 10/457,586, filed on Jun. 9, 2003, now abandoned.

(51) Int. Cl.
*C11D 3/50* (2006.01)

(52) U.S. Cl. ........................................ 510/102; 512/21
(58) Field of Classification Search ................ 510/102; 512/21
See application file for complete search history.

(56) References Cited

U.S. PATENT DOCUMENTS

| | | | | |
|---|---|---|---|---|
| 3,074,891 A * | 1/1963 | Kulka | ........................ | 424/76.2 |
| 3,074,892 A * | 1/1963 | Kulka | .......................... | 424/45 |
| 4,009,253 A * | 2/1977 | Schleppnik et al. | .......... | 424/45 |
| 4,045,551 A * | 8/1977 | Ueno et al. | ................. | 424/76.4 |
| 4,187,251 A * | 2/1980 | Schleppnik | .................. | 568/376 |
| 4,310,512 A * | 1/1982 | Schleppnik | ................ | 424/76.4 |
| 4,622,221 A * | 11/1986 | Schleppnik | ................ | 424/76.4 |
| 4,663,315 A * | 5/1987 | Hasegawa et al. | ......... | 424/76.3 |
| 5,066,640 A * | 11/1991 | Voss et al. | ..................... | 512/21 |
| 5,135,747 A * | 8/1992 | Faryniarz et al. | ........... | 424/401 |
| 5,658,580 A * | 8/1997 | Mausner | ..................... | 424/401 |
| 5,730,670 A * | 3/1998 | Ferrarin | ....................... | 474/79 |
| 5,843,192 A * | 12/1998 | Kirk et al. | ..................... | 8/137 |
| 6,197,288 B1 * | 3/2001 | Mankoo | .................... | 424/76.1 |
| 6,432,891 B1 * | 8/2002 | O'Connor | .................. | 510/106 |
| 6,610,648 B2 * | 8/2003 | McGee et al. | ................ | 512/21 |

* cited by examiner

*Primary Examiner*—John R. Hardee
(74) *Attorney, Agent, or Firm*—Norris McLaughlin & Marcus, PA

(57) ABSTRACT

A composition is provided for MOC that contains compounds with the structure

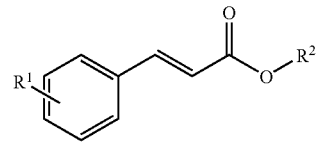

wherein
$R^1$ is a hydrogen, an alkyl, an alkoxy, or a substituted or unsubstituted aryl group;
$R^2$ is an alkyl having greater than 6 carbons, a substituted aryl, or unsubstituted aryl. Preferably these compounds have a low odor intensity.

These compounds may be used with other MOC ingredients that act synergistically or additively with them.

18 Claims, No Drawings

MALODOR COUNTERACTANT COMPOUNDS

This is a divisional application of allowed U.S. patent application Ser. No. 11/202,718, filed Aug. 12, 2005, which is a divisional application of U.S. application Ser. No. 10/457,586, filed Jun. 9, 2003, now abandoned.

FIELD OF THE INVENTION

The present invention relates to malodor counteractancy compositions. More particularly, the present invention relates to fragrance compositions containing one or more malodor counteractancy compounds.

BACKGROUND OF THE INVENTION

Malodors are offensive odors, which are encountered in the air and on many substrates such as fabrics, hard surfaces, skin, and hair. Malodors have either personal or environmental origin. For example sweat, urine, and feces malodors are personal in origin, whereas, kitchen, gasoline, cooking, tobacco smoke, etc. malodors are of environmental origin. While personal malodors are easily deposited on fabric, hair, and skin, environmental malodors also have a propensity to deposit on these substrates. Combinations of personal and environmental malodors make up a composite malodor, which has many oil soluble, water soluble, and solid components that have a vapor pressure at ambient temperatures, which is why humans can detect them.

Amines, thiols, sulfides, short chain aliphatic and olefinic acids, aldehydes, and esters form the largest and most unpleasant chemical groups found in sweat, household, and environmental malodors. These types of malodors typically include indole, skatole, and methanethiol found in toilet and animal odors; piperidine and morpholine found in urine; pyridine and triethyl amine found in kitchen and garbage odors, such as fish; hydrogen sulfide, nicotine, and various pyrroles found in cigarette smoke odors, and short chain fatty acids in axilla malodors.

Several approaches have been used to counteract malodors. These approaches include masking by superimposing the malodor with a pleasant stronger odor, cross-adaptation by blocking of the malodor olfactory receptors, suppression of the malodor by mixing with an ingredient that causes a negative deviation of Raoult's law, elimination of the malodor by chemical reaction, absorption of the malodor by a porous or cage-like structure, and avoidance of the formation of malodors by such routes as antimicrobials and enzyme inhibitors. All of these approaches are deficient, however, because they provide a perfumer with only limited options for malodor counteractants. Accordingly, there is still a need for additional and improved malodor counteractancy compositions.

It is known that fragrances may be designed to counteract malodors. The fragrance materials, which are most common to mask a malodor are those that contain a carbon-carbon double bond conjugated with one or more carbonyl groups. Aldehydes are the most commonly used materials of this class for malodor counteractancy, the most commonly used for deodorant properties are trimethyl hexanal, other alkyl aldehydes, benzaldehyde, and vanillin. For example, European Patent Application 0404470 discloses the use of fragrance materials with good malodor reduction efficacy, and European Patent Application 0545556 discloses mixtures of fragrance materials that mask malodors. The use of fragrance materials alone, however, may limit the types of fragrances a perfumer can create.

Other materials have also been shown to have malodor counteractancy (MOC) properties. Schleppnik, U.S. Pat. No. 4,622,221 ("Schleppnik '221") discloses the use of cyclohexyl alcohols and ester derivatives in room fresheners. Kulka, U.S. Pat. No. 3,074,891 discloses esters of alpha-, beta-unsaturated monocarboxylic acids as malodor counteractants. Kulka, U.S. Pat. No. 3,077,457 discloses fumaric acid esters as malodor counteractants. Schleppnik, U.S. Pat. No. 4,187,251 discloses alkyl cyclohexyl alkyl ketones as malodor counteractants. Schleppnik, U.S. Pat. No. 4,310,512 discloses the use of derivatives of acetic and propionic acids, and Schleppnik et al., U.S. Pat. No. 4,009,253 discloses the use of 4-cyclohexyl-4-methyl-2-pentanone as a malodor counteractant. These materials, however, are not capable of neutralizing all types of functional groups contained in malodor molecules. All of the U.S. patents discussed above are hereby incorporated by reference as if recited in full herein.

Unsaturated non-perfumery chemical compounds have also been shown to act as effective deodorants on the basis that many reactive odor-causing molecules may be eliminated by addition across the double bond. Unfortunately, many of the unsaturated compounds themselves have very unpleasant and offensive odors.

SUMMARY OF THE INVENTION

While all of the approaches set forth above are designed to mitigate malodors, none of them adequately eliminates the malodor. Accordingly, a need exists for compounds that counteract malodors alone, or in combination with other malodor counteractants. Ideally, the compounds should have little or neutral odors so that they may also be used in products that contain fragrance.

Accordingly, one embodiment of the invention is a composition containing a Class A compound of the formula:

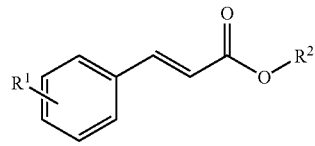

wherein $R^1$ is an hydrogen, an alkyl, an alkoxy, a substituted or unsubstituted aryl; and $R^2$ is an alkyl having more than 6 carbon atoms, an aryl or a substituted aryl, and the Class A compound exhibits a malodor counteractancy (MOC) effect.

Another embodiment of the invention is a process for dispersing a malodor counteractancy (MOC) composition into a space This process includes:

(a) incorporating into a consumer product a MOC composition containing a Class A compound of the formula:

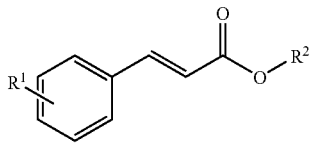

wherein
$R^1$ is an hydrogen, an alkyl, an alkoxy, a substituted or unsubstituted aryl; and
$R^2$ is an alkyl having more than 6 carbon atoms, an aryl or a substituted aryl; and
(b) dispersing an effective amount of the consumer product to achieve a MOC effect in the space.

A further embodiment of the invention is a process for imparting a MOC effect to a substrate. This process includes:
(a) contacting a substrate with a consumer product containing a Class A compound of the formula:

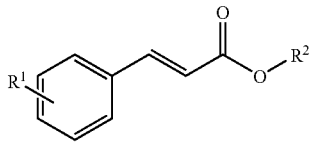

wherein
$R^1$ is an hydrogen, an alkyl, an alkoxy, a substituted or unsubstituted aryl; and
$R^2$ is an alkyl having more than 6 carbon atoms, an aryl or a substituted aryl, which Class A compound has a MOC effect.

Another embodiment of the invention is a fragrance composition containing:
(a) a Class A compound having a malodor counteractancy (MOC) effect of the formula:

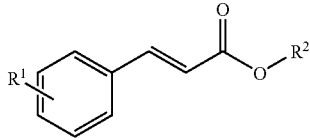

wherein
$R^1$ is an hydrogen, an alkyl, an alkoxy, a substituted or unsubstituted aryl; and
$R^2$ is an alkyl having more than 6 carbon atoms, an aryl or a substituted; and
(b) a fragrance.

DETAILED DESCRIPTION OF THE INVENTION

We have surprisingly found that certain aromatic unsaturated carboxylic esters wherein the unsaturation is conjugated to both the aromatic ring and the carbonyl group portion of the carboxylic ester counteract malodors. This malodor counteractancy effect is additive to that achieved by some classes of known malodor counteractancy, ingredients and, therefore, provides an additional advantage to e.g., perfumers who require low odor intensity or neutral odor malodor counteractancy compounds More surprisingly, these compounds may act synergistically with specific known MOC compounds.

As used herein, malodor counteractancy ("MOC") means the reduction of the perception of the offensiveness of a malodor or malodors to the human sense of smell. In the present invention, MOC is evaluated as set forth in the Examples. As used herein, a MOC effect is said to be "additive" when the malodor counteractancy effect of a MOC composition is equal to the sum of the malodor counteractancy effects of each MOC compound in the composition alone. An effect is said to be "synergistic" when the malodor counteractancy effect of a MOC composition is greater than the sum of the malodor counteractancy effects exhibited by each MOC compound in the composition alone.

The present invention provides a composition containing a compound or mixture of compounds having low odor intensity or neutral odor that counteracts malodors.

In the present invention, compounds having an aromatic unsaturated carboxylic ester, wherein the unsaturation is conjugated to both the aromatic ring and the carbonyl group of the carboxylic ester have been found to counteract malodors. These molecules have the structure shown below, and are designated herein as Class A compounds:

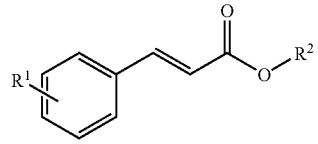

wherein $R^1$ is an hydrogen, an alkyl, an alkoxy, an aryl, or a substituted aryl, preferably $R^1$ is H, a C1 to C8 alkyl, a C1 to C8 alkoxy, or an aryl; and
$R^2$ is an alkyl having greater than 6 carbon atoms, an aryl, or a substituted aryl group, preferably, $R^2$ is a C6 to C12 alkyl or an aryl.

Preferably, the Class A compounds have a low odor intensity. As set forth in more detail in Example 5, in the present invention, compounds with low odor value are preferred because they are easier to incorporate into a fragrance composition. Thus, as used herein, a compound with a low odor intensity is defined as one having an Odor Value of less than 1000, preferably an Odor Value of less than 500. In the present invention, "Odor Value" is the quantity of compound in the headspace in nanograms per liter divided by its perception threshold as in nanograms per liter. Odor Value is determined by the methods disclosed by Nuener-Jehle and Etzweiler (Neuner-Jehle N. and Etzweiler F., Perfumes Art Science & Technology, Chapter 6, p 153, Elsevier Science Publishers LTD, England.)

In the present invention, the Class A compounds may be combined with certain Class B MOC compounds to provide an additive MOC effect. As used herein, the Class B MOC compounds that are combinable with the Class A compounds of the present invention have an Odor Value of less than 1000, preferably less than 500. Class B compounds that are useful in the present invention (a) have a MOC effect of less than 1000, preferably less than 500 and (b) when combined with a Class A compound of the present invention exhibit at least an additive, preferably a synergistic MOC effect as determined using the methods set forth in one of the Examples below. In the present invention, when combinations of Class A and Class B compounds are used, the composition should also have an Odor Value of less than 1000, preferably less than 500.

Thus, in the present invention, the Class B MOC compounds include, for example, aliphatic alpha unsaturated dicarboxylic esters wherein the double bonds are bracketed between carbonyl groups, cycloalkyl tertiary alcohols, esters of alpha-, beta-, unsaturated monocarboxylic acids, and 4-cyclohexyl4-methyl-2-pentanone. Preferably, the Class B compounds are geranyl crotonate, dihexyl fumerate, cyclohexylethylisobutyrate, and cyclohexylethylhexanoate. Moreover, mixtures of Class B compounds may also be used, such as for example a mixture of dihexyl fumerate

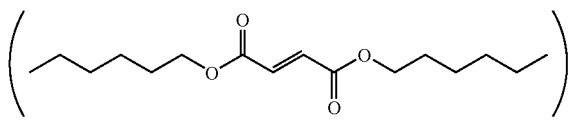

and geranyl crotonate

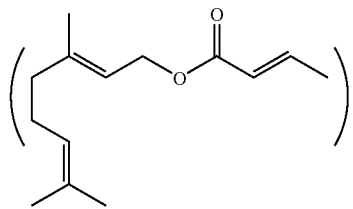

Optionally, the MOC compositions as defined above (i.e., compositions containing a novel Class A compound as set forth above and compositions containing a mixture of Class A and B MOC compounds) may be used in combination with a fragrance, preferably with a fragrance that has a MOC effect. For purposes of the present invention, a fragrance that has a MOC effect is a mixture of fragrance ingredients, which in combination reduce the perception of a malodor as measured by one of the methods set forth in the examples. In the present invention, the fragrance ingredients may be selected from alcohols, aldehydes, ketones, esters, acetals, oximes, nitriles, ethers, essential oils, and mixtures thereof.

The amount of a Class A MOC compound alone or a mixture of Class A and Class B compounds required for effective malodor counteractancy depends upon the type of product into which such a compound or mixture of compounds is incorporated. For example, if no fragrance is present in the product, then a minimum amount of a Class A MOC compound is required, such as 0.1% (wt), preferably 0.2% (wt). In a product containing a fragrance, the Class A compound according to the present invention is required to be present at a minimum of 0.01% (wt), preferably 0.025% (wt). These same ranges also apply to fragrance-less compositions containing mixtures of MOC compounds.

When a fragrance is used in a MOC composition according to the present invention, more of the Class A and/or B MOC compound(s) will typically be required. For example, when a fragrance is used, the MOC compounds are present in the composition at greater than 1% (wt) of the fragrance, preferably at greater than 5% (wt) of the fragrance.

In compositions containing a mixture of Class A and B compounds, the ratio of Class A to Class B compounds is 1:99 to 70:30, preferably 5:95 to 70:30.

Antimicrobial agents may be incorporated into the present compositions. Such antimicrobial agents include, for example, metal salts such as zinc citrate, zinc oxide, zinc pyrethiones, and octopirox; organic acids, such as sorbic acid, benzoic acid, and their salts; parabens, such as methyl paraben, propyl paraben, butyl paraben, ethyl paraben, isopropyl paraben, isobutyl paraben, benzyl paraben, and their salts; alcohols, such as benzyl alcohol, phenyl ethyl alcohol; boric acid; 2,4,4'-tichloro-2-hydroxy-diphenyl ether; phenolic compounds, such as phenol, 2-methyl phenol, 4-ethyl phenol; essential oils such as rosemary, thyme, lavender, eugenol, geranium, tea tree, clove, lemon grass, peppermint, or their active components such as anethole, thymol, eucalyptol, farnesol, menthol, limonene, methyl salicylate, salicylic acid, terpineol, nerolidol, geraniol, and mixtures thereof.

In the present invention, malodor adsorbers may also be incorporated into the present MOC compositions. As used herein, "malodor adsorbers" are any material that adsorbs malodor in sufficient quantities to provide a reduction in malodor perception, and which do not reduce the MOC effectiveness of the compositions of the present invention. Such malodor absorbers include, for example, inorganic absorbents, including molecular sieves, such as zeolites, silicas, aluminosilcates, and cyclodextrins; and organic absorbents, such as for example, activated charcoal, dried citrus pulp, cherry pit extract, corncob, and mixtures thereof.

The MOC compositions of the present invention may be incorporated into various products, e.g., consumer products, such as for example the products set forth in more detail below.

The present invention also includes a process for dispersing the MOC compositions of the present invention into a space. This process includes incorporating into a composition, such as for example, a consumer product, a MOC composition containing a Class A compound as defined above and dispersing an effective amount of the consumer product to achieve a MOC effect in the space. In addition, the MOC composition may contain a mixture of Class A and Class B compounds as defined above.

As used herein, an "effective amount" of the composition, e.g., consumer product, will vary depending upon the intended use, the composition used, the ambient conditions, and other well known variables. Using the examples provided below, one skilled in the art may judge the appropriate amounts of the MOC compositions to be used in order to dispense an effective amount of, e.g. the consumer product, into the space.

As used herein, "consumer products" include, for example, sprays, candles, gels, plug-in electrical devices and battery-operated devices for introducing compositions into spaces, and liquid wicking systems. In the present invention, the sprays may be aqueous or non-aqueous. The candles and gels of the present invention may be opaque, translucent, or transparent, and may contain optional ingredients to enhance their appearance. The plug-in and battery-operated devices may include devices that vaporize the fragrance by heat, evaporation, or nebulization.

In this process, the dispersing step may be achieved by, for example spraying, atomizing, and volatilization. Typically, the MOC composition is then dispersed into, for example, rooms, closets, chests, and draws.

The present invention also provides a process for imparting a MOC effect to a substrate. This process includes contacting a substrate with a composition, such as a consumer product, containing a Class A compound that has a MOC effect. In addition, Class B compounds that have a MOC effect as defined above may also be combined with the Class A compounds. In this process, the substrate may be either hair or skin. And, the consumer product used in this process may be any one of the products defined below.

The products of the present invention that are to provide MOC when applied to the skin may include, for example, talcum powder, deodorants and antiperspirants in the form of sprays, soft solids, and solids, lotions, and oils.

In the present invention, the Class A and Class B compounds may be incorporated into products that are used to clean the skin, and to provide a MOC to the skin. Such products include, for example, soap, syndet, and combination soap and syndet personal wash bars, personal wash liquids, and personal wipes.

As noted above, the Class A and Class B compounds may be incorporated into products, and used in processes, that are to provide a MOC effect to the hair. Such products, include for example, shampoos, conditioners, styling sprays, mousses, gels, hair wipes, hair sprays, and hair pomades.

The products and processes of this invention that are to provide a MOC effect by treating a substrate may include or utilize, for example, fabric washing liquids and powders, fabric conditioners, wipes, dishwashing liquids and powders, hard surface cleaning liquids and powders, and aqueous and non-aqueous sprays.

The present invention also provides fragrance compositions containing a Class A compound as defined above having a MOC effect in combination with a fragrance. In this composition, the fragrance may be any art recognized fragrance composition, preferably one also having a MOC effect. The fragrance composition may further include a Class B compound as defined above having a MOC effect, wherein the MOC effect of the Class A and Class B compounds is additive, preferably synergistic.

The fragrance compositions may include any of the Class A compounds set forth in Table 1 below. Preferably, the Class A compound is OMC. If a mixture of Class A and Class B compounds is desired, preferably the Class B compounds will be selected from aliphatic alpha unsaturated dicarboxylic esters wherein the double bonds are bracketed between carbonyl groups, cycloalkyl tertiary alcohols, esters of alpha-, beta-, unsaturated monocarboxylic acids, and 4-cyclohexyl-4-methyl-2-pentanone. Preferably, the Class. B compound is selected from dihexyl fumerate, cyclohexylethylisobutyrate, and cyclohexylethylhexanoate. More preferably, the Class B compound is dihexyl fumerate. Thus, when a mixture of Class A and Class B compounds is desired, it is preferred that the Class A compound be OMC and that the Class B compound be dihexyl fumerate.

The following examples are provided to further illustrate the compounds, compositions, and processes in accordance with the invention. These examples are illustrative only and are not intended to limit the scope of the invention in any way. In these examples, all % are % (wt), unless otherwise noted.

EXAMPLES

Example 1

MOC Effect—Class A Compounds

100 μl of synthetic axilla malodor was placed onto cotton pads. 0.4 g of an ethanolic solution containing 10% (wt) of a test compound identified in Table 1 was placed on each axilla malodor treated cotton pad. Each pad was allowed to dry 15 for minutes, and then evaluated using a 10-member panel after 3 hours. The test cotton pads were randomized, and each panelist was asked to check a box that represented the strength of the axilla malodor using the following scale:

| Overpowering | 5 |
| Strong | 4 |
| Moderate | 3 |
| Weak | 2 |
| Not detectable | 1 |

TABLE 1

| Compound Number | Structure |
|---|---|
| GR-84-6495/000 | 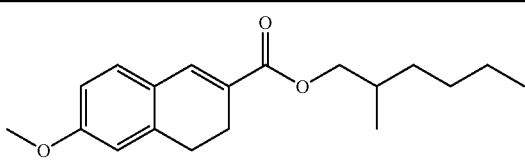 |
| GR-84-6924/000 | 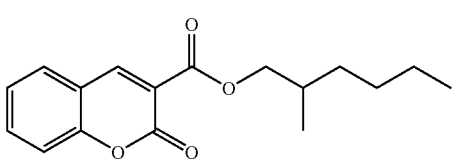 |
| GR-85-2280/001 | 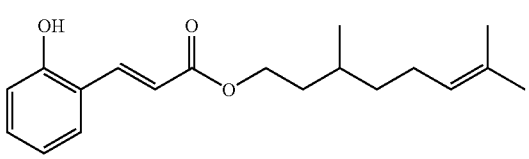 |

TABLE 1-continued

| Compound Number | Structure |
| --- | --- |
| GR-85-1407/000 | (structure) |
| GR-85-2661/000 | (structure) |
| GR-85-3260/000 | (structure) |
| GR-85-3427/000 | (structure) |
| GR-85-3428/000 | (structure) |
| GR-85-3429/000 | (structure) |
| GR-85-3565/000 | (structure) |
| Benzyl Cinnamate (BC) | (structure) |
| Phenylethylcinnamate (PC) | (structure) |

TABLE 1-continued

| Compound Number | Structure |
| --- | --- |
| Octyl methoxy cinnamate OMC | (structure shown) |

The results of the panel determinations are presented in Table 2 below:

TABLE 2

| Compound Code | Class A + Malodor | Malodor Alone |
| --- | --- | --- |
| GR 85-1407 | 3.4 | 3.9 |
| GR 85-2280 | 2.9 | 3.9 |
| GR 85 3428 | 2.8 | 3.9 |
| GR 85-3260 | 3.5 | 3.9 |
| GR 85-3565 | 2.7 | 3.7 |
| GR 85-3429 | 3.3 | 3.7 |
| GR85-2661 | 2.9 | 3.9 |
| GR 85-3427 | 3.0 | 3.9 |
| GR 85-6924 | 2.9 | 3.9 |
| GR 85-6495 | 2.8 | 3.9 |
| OMC | 2.6 | 4.0 |
| BC | 2.3 | 4.1 |
| PC | 2.2 | 4.3 |

As Table 2 demonstrates, all Class A compounds reduced the perception of the malodor on the test pads. Based on these results, although not wishing to be bound by a particular theory, there appeared to be a benefit, i.e., an enhancement of malodor counteractancy, when the structure of the test compound enhanced electron donation to the carbonyl group.

Example 2

MOC Effect: Class A and DHF Compound Mixtures

In this example, the MOC effect of various mixtures of a Class A MOC compound and a Class B MOC compound (i.e., dihexyl fumerate as disclosed in Kulka, U.S. Pat. No. 3,074,892) were evaluated using the same test and malodor evaluation procedures as set forth in Example 1. Each test solution contained 5% (wt) DHF and 5% (wt) of the Class A compound identified in Table 3. The MOC effect was evaluated as in Example 1. The results of the MOC evaluation are presented in Table 3 below.

TABLE 3

| Class A Compounds | 50% DHF/50% Class A | Malodor Alone |
| --- | --- | --- |
| GR 85-1407 | 3.0 | 3.9 |
| GR 85-2280 | 3.1 | 3.9 |
| GR 85-3428 | 3.3 | 3.9 |
| GR 85-3260 | 2.9 | 3.9 |
| GR 85-3565 | 3.1 | 3.7 |
| GR 85-3429 | 2.8 | 3.7 |
| GR85-2661 | 2.4 | 3.9 |
| GR 85-3427 | 3.3 | 3.9 |
| GR 85-6924 | 2.5 | 3.9 |
| GR 85-6495 | 3.0 | 3.9 |
| OMC | 2.3 | 4.0 |

As the data above indicate, the mixtures of Class A compounds with DHF, in, general, provided a better MOC effect compared to the Class A compounds alone, i.e. at least an additive effect was demonstrated.

Example 3

MOC Effect: OMC and Class B Compound Mixtures

Various mixtures of OMC (a Class A Compound) and a Class B compound (i.e., various cyclohexyl esters as disclosed in Schleppnik '221) as identified in Table 4 below were made according to the procedure set forth in Example 1. The MOC of each mixture was evaluated using the procedure set forth in Example 1. The results of the MOC evaluation are set forth in Table 4 below.

TABLE 4

| Test Compound B | Structure | Control (No A or B) | 10% test (Compound B Alone) | 5% OMC + 5% Compound B | 10% OMC (Alone) |
| --- | --- | --- | --- | --- | --- |
| Dihexyl Fumerate | (structure shown) | 4.0 | 2.6 | 2.3 | 2.6 |

TABLE 4-continued

| Test Compound B | Structure | Control (No A or B) | 10% test (Compound B Alone) | 5% OMC + 5% Compound B | 10% OMC (Alone) |
|---|---|---|---|---|---|
| Cyclohexyl-ethyliso-butyrate | 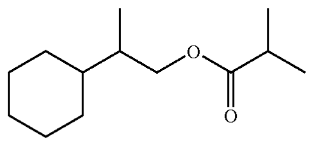 | 4.1 | 2.2 | 2.2 | 3.0 |
| Cyclohexyl-ethylhexanoate | 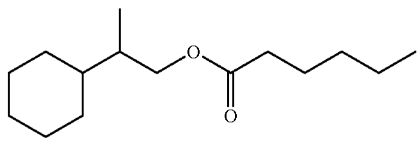 | 3.9 | 2.2 | 2.2 | 3.1 |

As the data in Table 4 indicate, OMC acts at least additively with the Class B compounds (Test Compound B).

Example 4

MOC of Sweat Malodor on Fabric Substrates

The following fabric treatment solutions were prepared:
1. A solution of ethanol and Cremophor (a hydrogenated ethoxylated castor oil marketed by BASF Corp., Mount Olive, N.J.) containing 10% (wt) of dihexyl flimerate (DHF).
2. A solution of ethanol and Cremophor containing 10% (wt) of OMC.
3. A solution of ethanol and Cremophor containing 5% (wt). of DHF+5% (wt) OMC:

Five (5) fabric swatches were prepared, and labeled A-E. Swatch A was designated as the control swatch with no malodor. 100 µl of sweat malodor was placed in the middle of swatches B-E. Swatch B was designated as the control swatch for the malodor. The swatches were allowed to equilibrate with the malodor for 20 minutes. Onto swatches C-E, the following solutions were sprayed:

TABLE 5

| Swatch No. | DHF/MOC | DHF | MOC |
|---|---|---|---|
| C | Soln. 3 | | |
| D | | Soln. 2 | |
| E | | | Soln. 1 |

The malodor intensity on the cotton swatches was evaluated as follows:

The malodor intensity on swatch B (Malodor Control) was identified as a 5 (overpoweringly strong) on the scale of 1-5 set forth below at every time point, and the rest of swatches were evaluated based on that standard.

| Score | Malodor Intensity |
|---|---|
| 5 | Overpoweringly Strong |
| 4 | Strong |
| 3 | Moderate |
| 2 | Weak |
| 1 | Not Detectable |

TABLE 6

| | Swatch C | Swatch D | Swatch E |
|---|---|---|---|
| 30 mins | 2.6 | 3.4 | 3.3 |
| 3 hrs | 2.6 | 3.0 | 3.3 |

As the data in Table 6 indicate, both OMC and DHF alone had a MOC effect. When mixed, these compounds had a MOC effect that was at least as good, if not better than, either compound alone.

Example 5

Scaling of Odor Value and Ease of Incorporation into Perfume

To provide standards by which "neutral" odor and low odor values are judged, a perfumer was asked to scale aroma chemicals identified in Table 7 below based on how easy was it to incorporate the compound into a fragrance composition at 10% (wt.) without a significant distortion of the fragrance note.

The following scale was used to evaluate the "ease" with which certain compounds could be incorporated into a fragrance composition, with "5" being difficult to incorporate into the fragrance composition without significant fragrance distortion and "1" being very easy without significant fragrance distortion:

5—Difficult
3—Acceptable
1—Very easy

The results of this evaluation are presented in Table 7 below:

TABLE 7

| MATERIAL | SCORE |
|---|---|
| Cinnamic Aldehyde | 5 |
| | (Odor Value = 12000) |
| Hexyl Benzoate | 3 |
| | (Odor Value = 1000) |
| Hexyl Cinnamic Aldehyde | 2 |
| | (Odor Value = 384 |
| Dipropylene Glycol | 1 |
| | (OV = 40) |
| GR-84-6495/000 | 1 |

TABLE 7-continued

| MATERIAL | SCORE |
|---|---|
| GR-84-6924/000 | 1 |
| GR-85-2280/001 | 4 |
| GR-85-1407/000 | 3 |
| GR-85-2661/000 | 3 |
| GR-85-3260/000 | 1 |
| GR-85-3427/000 | 2 |
| GR-85-3428/000 | 2 |
| GR-85-3429/000 | 2 |
| GR-85-3565/000 | 2 |
| OMC | 1 |

Based on this data, compounds with an Odor Value of below 1000, preferably below 500, are selected for use as MOC compounds in the present invention.

Example 6

Effect of OMC on a Fragrance Composition

In this example, the ability of a fragrance composition, with and without OMC, to reduce the smell of axilla malodor was evaluated.

Axilla treated pads were sprayed with both 1% (wt) fragrance GJG817AGJ and 1% (wt) fragrance GJG817AGJ containing 5% (wt) OMC. Sensory evaluation showed fragrance GJG817AGJ reduced the perception of tobacco smoke by 32 to 36% while the mixture of fragrance GJG817AGJ and OMC reduced the perception of tobacco smoke by 44 to 51%.

As noted above, malodor testing was conducted with fragrance composition GJG817AGJ whose formula is shown below.

| Ingredient | Percent |
|---|---|
| Allylamyl Glycoate | 0.40 |
| Coumarin | 0.55 |
| Cyclogalbanate | 0.40 |
| Dihydro Myrcenol | 10.55 |
| Ebanol | 0.55 |
| Ethyl Linalool | 1.90 |
| Hedione | 43.35 |
| Hexenol-3-cis | 0.20 |
| Ionone beta | 3.05 |
| Iso E super | 13.25 |
| Lilial | 2.80 |
| Linalool | 12.45 |
| Phenylethyl Alcohol | 3.40 |
| Tropional | 4.15 |
|  | 100.00 |

The following test solutions were prepared and placed in small pump sprayers:

Test solution A: 1% (wt) fragrance (0.1 grams, GJG817AGJ) in 9.9 grams ethanol.

Test solution B: 1% (wt) fragrance (0.1 grams of 95% (wt) GJG817AGJ+5% (wt) OMC) in 9.9 grams ethanol).

100 ul of axilla malodor were placed onto 5×5 cm cotton pads. Then, 0.15 g of the material to be tested was sprayed onto the axilla treated cotton pads. The pads were allowed to dry for 15-20 minutes under a fume hood. Each pad was placed into blind coded Petri-dishes.

Sensory evaluations were conducted by asking a 12 member panel to rate the perceived intensity of the axilla malodor present on a control using scale of 1-5 as shown below 3 hours after addition of the test solutions. The panelists were randomly presented with the test materials and again asked to rate the perceived intensity of axilla malodor.

TABLE 8

| 3 hour Axilla Malodor | | |
|---|---|---|
| Control | Fragrance | Fragrance + OMC |
| 3 | 3 | 1 |
| 4 | 3 | 2 |
| 3 | 1 | 1 |
| 4 | 2 | 2 |
| 4 | 2 | 3 |
| 3 | 2 | 3 |
| 3 | 3 | 1 |
| 4 | 2 | 2 |
| 5 | 3 | 2 |
| 3 | 3 | 2 |
| 4 | 3 | 1 |
| 4 | 2 | 3 |
| Average 3.6 | 2.3 | 1.8 |
| % Reduction | 36.0 | 51.4 |

Example 7

Effect of the Presence of OMC in a Fragrance on Tobacco Smoke

The ability of a fragrance, with and without OMC, to reduce the smell of tobacco smoke on hair was determined.

Hair tresses previously exposed to tobacco smoke were sprayed with either 1% (wt) fragrance (GJG817AGJ) alone or 1% (wt). fragrance (GJG817AGJ) containing 5% (wt) OMC. Sensory evaluation showed fragrance reduced the perception of tobacco smoke by 31 to 34% while the mixture of fragrance and OMC reduced the perception of tobacco smoke by 45 to 46% compared to control (no fragrance/No OMC).

The following test solutions were prepared and placed in small pump sprayers.

Test solution A: 1% Fragrance (0.1 grams GJG817AGJ) in 9.9 grams ethanol).

Test solution B: 1% Fragrance (0.1 grams (95% GJG817AGJ+5% MOC) in 9.9 grams ethanol.

Clean hair tresses weighing 5.0 g each were prepared for use in this experiment by hanging in a small odor booth. A lit cigarette was placed in the booth for 10 minutes and then extinguished. The hair tresses were left in the booth for an additional 5 minutes, then removed.

With a pump spray, each tress was sprayed once on the back and again in the front (total amount delivered being 0.15 gram) with either Test Solution A or B. The treated tresses were allowed to dry for 5 minutes, and then were placed in a labeled Petri dish for three hours.

The ability of each Test Solution to counteract the tobacco smoke odor was evaluated using a 20-member panel. Each panelist was asked to rate the intensity of the malodor (tobacco smoke) present on the control using a Labeled Magnitude Scale (LMS) scale. (See diagram below). The panelists were then randomly presented with test samples generated by treatment of the hair tresses with Test Solution A or B, and asked to rate the intensity of the malodor (tobacco smoke) on the hair tresses after three hours.

The Labeled Magnitude scale (LMS) is a semantic scale of perceptual intensity characterized by a quasi-logarithmic scaling of its verbal labels. The LMS is a protocol selected from the literature as having the least response bias. It allows the subject to scale and rate the intensity of stimuli using natural language descriptors. With this scale, ratings of odor intensities are made in the context of all previous experience with odors. The subject task consists in sniffing the stimuli and then rating its intensity by indicating, on the scale, where each odor lies.

The position of the verbal labels on the LMS, as percentage of full scale length, are: barely detectable, 1.4; weak, 6.1; moderate, 17.2; strong, 53.2; strongest imaginable, 100.

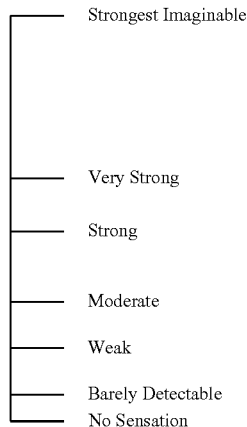

The following instruction was given to each panelist before starting the experiment:

In making your judgements of intensity of odor sensations, you should rate the stimuli relative to other odor sensations of all kinds that you have experienced. This includes such varied sensations as the strong smell of rotting garbage, the odor of a subtle perfume, or the tingling/burning from smoky air. Thus, "strongest imaginable" refers to the most intense odor sensation that you can imagine experiencing.

REFERENCES

Barry G. Green, Gregory S. Saffer and Magdalena M. Gilmore. Derivation and evaluation of a semantic scale of oral sensation magnitude with apparent ratio properties. *Chemical Senses*. Vol. 18, n 6, pp 683-702,1993.

Cf. Barry G. Green, Pamela Dalton, Beverly Cowart, Greg Shaffer, Krystyna Ranking and Jennifer Higgins. Evaluating the *Labeled Magnitude Scale* for measuring sensations of taste and smell. Chemical Senses. Vol. 21, pp 323-334, 1996.

TABLE 9

| 3 hours Tobacco Smoke on Hair | | |
|---|---|---|
| Control | 1% Fragrance | Fragrance + MOC |
| 4 | 3 | 1 |
| 3 | 3 | 3 |
| 4 | 2 | 3 |
| 4 | 2 | 2 |
| 3 | 3 | 3 |
| 5 | 3 | 2 |
| 4 | 2 | 2 |
| 4 | 2 | 2 |
| 4 | 3 | 2 |
| 3 | 2 | 2 |

TABLE 9-continued

| 3 hours Tobacco Smoke on Hair | | |
|---|---|---|
| | Control | 1% Fragrance | Fragrance + MOC |
| | 4 | 3 | 2 |
| | 5 | 3 | 2 |
| Average | 3.9 | 2.5 | 2.1 |

Example 8

Effect of OMC as a Malodor Counteractant on Cotton Fabric

The ability of OMC to reduce the malodor intensity of tobacco smoke, onion, and garlic solutions on cotton fabric was determined.

Cotton cloth pads were evaluated by 20 panelists to determine how well OMC reduced the perceived odor of tobacco smoke, onion, and garlic solutions on cotton fabric.

TABLE 10

| Malodor | OMC | CONTROL |
|---|---|---|
| Smoke | 1.8 | 4.5 |
| Onion | 2.7 | 4.0 |
| Garlic | 2.6 | 4.8 |

Onion and Garlic

Samples were prepared fresh before each evaluation. A solution of 2.5% (wt) garlic and a solution of 2.5% (wt) onion were both made using 39C alcohol as the solvent. Briefly, 0.4 g of the garlic and onion solutions were each sprayed onto cotton towel pads (100% cotton, 5×5 cm). 0.4 g of a test solution containing 5% OMC in ethanol were then sprayed on the onion and garlic-treated cotton pads. The pads were allowed to dry for 15-20 minutes under a fume hood. Each pad was then placed in a blind coded Petri-dish.

Controls were prepared from cotton pads, which were treated only with the garlic or onion solution (i.e., no OMC test solution).

The effect of the test solutions on the garlic or onion odors were evaluated by asking a 20-member panel to rate the intensity of the malodor present on the controls and on the treated fabrics using a scale of 1-5 as shown below three hours after the preparation of each sample. The results are provided in Table 10 above. The data are average values from the scores by each of the 20 panelists.

Score
1 Overpowering
2 Strong
3 Moderate
4 Weak
5 Not detectable

Tobacco Smoke

Samples were prepared fresh before each evaluation. Clean pieces of fabric were treated with smoke by placing each fabric piece in a smoked filled environment for 10 minutes. Each piece of fabric was sprayed with 0.4 gram of the 5% (wt) OMC in ethanol test solution set forth above in the garlic and onion example. The treated fabric pieces were left to dry for 15 minutes, and then wrapped in foil.

Controls were prepared from a smoke-treated piece of cloth that was not sprayed with a test solution.

The fabric pieces were evaluated in the same way as described above in the onion and garlic example. The results are presented above also in Table 10.

The invention being thus described, it will be obvious that the same may be varied in many ways. Such variations are not to be regarded as a departure from the spirit and scope of the invention and all such modifications are intended to be included within the scope of the following claims.

What is claimed is:

1. A composition comprising a class A compound selected from the group consisting of the compounds represented by the following structures:

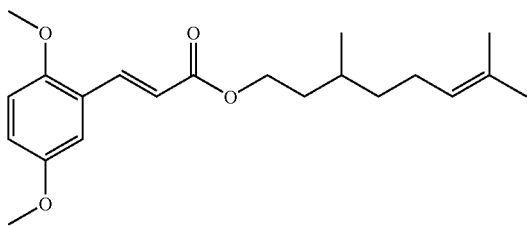

and further comprising a class B MOC compound selected from the group consisting of 4-cyclohexyl-4-methyl-2-pentanone, and the compounds represented by the following structures:

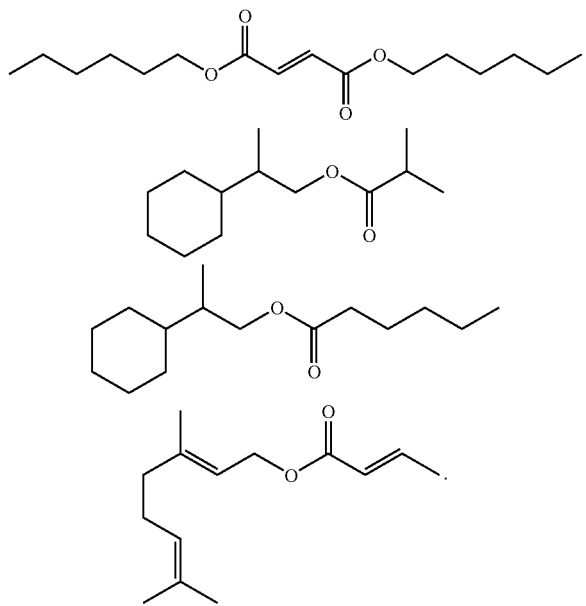

2. A composition according to claim 1 wherein the the class A compound has an Odor Value of less than 1000.

3. A composition according to claim 1 wherein the composition has an Odor Value of less than 1000.

4. A composition according to claim 1 wherein the Class B compound is dihexyl fumarate.

5. A composition according to claim 1 wherein the Class B compound is geranyl crotonate.

6. A composition according to claim 1 wherein the Class B compound is a mixture of dihexyl fumarate and geranyl crotonate.

7. A composition according to claim 1 wherein the MOC compounds are present in at least 0.01% (wt) in a formulation containing no fragrance.

8. A composition according to claim 7 wherein the MOC compounds are present at 0.025% (wt) in a formulation containing no fragrance.

9. A composition according to claim 1 further comprising a fragrance.

10. A composition according to claim 1 wherein the fragrance has a MOC effect.

11. A composition according to claim 10 wherein the MOC compounds are present in the composition at greater than 1% (wt) of the fragrance.

12. A composition according to claim 11 wherein the MOC compounds are present in the composition at greater than 5% (wt) of the fragrance.

13. A composition according to claim 1 further comprising an antimicrobial agent.

14. A composition according to claim 1 further comprising a malodor absorber.

15. A fragrance composition comprising:
(a) a Class A compound as defined in claim 1, and further comprising a Class B MOC compound selected from dihexyl fumarate, geranyl crotonate and mixtures thereof, and
(b) a fragrance.

16. A consumer product selected from the group consisting of:
sprays, candles, gels, plug-in electrical devices for introducing said compositions into a space, battery operated devices for introducing a said compositions into a space, and liquid wicking systems; said composition comprising a Class A compound as defined in claim 1 and a Class B compound as defined in claim 1.

17. A product for application to the skin selected from the group consisting of: talcum powder, deodorant, antiperspirant, lotions, oils, soap, syndet, personal wash bar, personal wash liquid, personal wipe; said composition comprising:
a Class A compound and a class B compound as defined in claim 1, and the Class A compound exhibits a malodor counteractancy (MOC) effect.

18. A product for application to the skin selected from the group consisting of: shampoos, conditioners, styling sprays, mousses, gels, hair wipes, hair sprays, and hair pomades; said composition comprising a Class A compound and a class B compound as defined in claim 1, and the Class A compound exhibits a malodor counteractancy (MOC) effect.

* * * * *